United States Patent [19]

Aitken et al.

[11] 4,295,930

[45] Oct. 20, 1981

[54] ALKOXYLATED DIOXOLANES AS PAPER SIZING AGENTS

[75] Inventors: Thomas Aitken, Chicago; David J. Kowalski, Clarendon Hills; K. G. Srinivasan, Oak Park, all of Ill.

[73] Assignee: Nalco Chemical Company, Oak Brook, Ill.

[21] Appl. No.: 130,666

[22] Filed: Mar. 17, 1980

[51] Int. Cl.³ .............................................. D21H 3/02
[52] U.S. Cl. ........................... 162/158; 260/340.9 R; 568/496; 568/497
[58] Field of Search ............. 162/158, 164 EP, 164 R, 162/168 N, 175; 260/340.9 R; 568/496, 497; 427/395; 8/116.4

[56] References Cited

U.S. PATENT DOCUMENTS

| | | | |
|---|---|---|---|
| 2,211,976 | 8/1940 | Hubert et al. | 427/394 |
| 2,242,051 | 5/1941 | Beck | 427/394 |
| 3,127,418 | 3/1964 | Koester | 260/340.9 R |
| 3,821,064 | 6/1974 | Wurzburg | 162/158 |

*Primary Examiner*—William F. Smith
*Attorney, Agent, or Firm*—John G. Premo; Robert A. Miller; Robert A. Wilkes

[57] ABSTRACT

This invention concerns a new class of compositions for the sizing of paper and the method of treating paper using such compositions. Such new compositions comprise the reaction products of glyoxal and a hydrophobe which contains at least one hydroxyl group. Such compositions can be used either for internal or surface sizing.

41 Claims, No Drawings

ALKOXYLATED DIOXOLANES AS PAPER SIZING AGENTS

BACKGROUND

Paper is sized to resist the penetration of liquids. This invention is concerned with the sizing of paper to resist penetration by water and aqueous solutions.

Paper can either be surface sized or it can be sized internally. Internal sizing is accomplished by the application of a sizing agent to the pulp slurry prior to formation of the paper sheet. Surface sizing, on the other hand, entails application of the sizing agent to the surface of a formed paper sheet. Internal and surface sizing are discussed in J. P. Casey, Pulp & Paper, Chemistry and Chemical Technology, Second Edition, Volume II, Interscience Publishers, Inc., New York, 1960.

For well over a century, internal sizing operations have employed rosin in combination with alum. Various improvements in the rosin-alum treatment have been made.

More recent internal sizing agents include wax emulsions, stearates, alkylketene dimers and alkenyl succinic anhydrides. Most of these new sizes are described in TAPPI Monograph Series 33, "Internal Sizing of Paper and Paperboard," Mack Printing Company/Easton, PA, 1971.

Current commercial internal sizing agents have important individual drawbacks. For example, rosin requires alum and an acid pH in papermaking. Alkylketene dimers give best performance in a non-acid system. Alkenyl succinic anhydrides cannot be produced as stable emulsions and require special emulsification at the site of use. Some other sizes are less efficient or have other particular drawbacks.

OBJECTS

It is an object of this invention to provide new efficient sizing agents useful in both surface and internal sizing of paper.

Another object of this invention is to provide sizing agents effective against acid, neutral and alkaline solutions.

A further object is to provide sizing agents which can be used over the pH range normally encountered in papermaking.

Yet another object is to provide sizing compositions in ready-to-use form.

THE INVENTION

The invention is a class of paper sizing compositions and the method of application to paper furnishes. Such compositions comprise the acid-catalyzed reaction product of glyoxal and a hydrophobe containing at least one hydroxyl group.

We are aware of U.S. Pat. No. 2,242,051, wherein H. Beck teaches a process for producing water-repellent textile materials by treatment of such materials with the acid-catalyzed reaction product of fatty alcohols and glyoxal. Webster's Third International Dictionary defines "textiles" as "cloth, woven or knit cloth, fiber, filament or yarn used in making cloth."

An earlier application, Ser. No. 893,639, since abandoned, taught the reaction of aqueous 40% glyoxal with hydrophobic alcohols at acid pH and the method of wet end and surface application to paper to provide sizing. Since that application was abandoned, we have now:

(a) established predominant chemical structures of our glyoxal-hydrophobic alcohol sizes (b) shown that appreciably higher sizing performance can be realized for use of aqueous glyoxal of appreciably above 40% concentration (c) shown that for use of such higher concentration glyoxal, further outstanding improvement in paper sizing performance can be realized by increasing the ratio of glyoxal to hydroxyl hydrophobe to levels not taught in the earlier art.

(d) determined that the active ingredients for optimized sizing, either internal or surface, are glyoxal-hydrophobe reaction products which are dimeric or trimeric dioxolanes.

Gyloxal

Although monomeric glyoxal can be produced in the laboratory, generation of such glyoxal is generally impractical for industrial purposes. We prefer to use aqueous glyoxal such as commercial 40% or 80% glyoxal or other concentrations as attained by stripping or adding water from or to commercially availably glyoxals.

The Hydrophobe

The hydrophobe will be chosen from the group consisting of:

(a) linear and branched, saturated and unsaturated fatty alcohols containing from 10–30 carbon atoms; and (b) esters formed from the esterification of a polyol containing from 2–6 hydrocarbon atoms with a fatty acid containing from 10–30 carbon atoms wherein the resulting esters contain at least one free hydroxyl group.

Preferable hydrophobes include such fatty alcohols as cetyl alcohol, myristyl alcohol, stearyl alcohol, decanol, dodecanol and olyeyl alcohol and esters such as sorbitan tristerearate and pentaerythritol disterarate. An especially preferred hydrophobe is a commercially available blend of $C_{16}$–$C_{20}$ linear alcohols known as Alfol 16-20 H+.

Reactant Ratios

In reacting the glyoxal and the hydrophobe, the ratio of glyoxal to hydrophobe should be from 0.1 mole to 6.0 mole of glyoxal to each hydroxyl group in the hydrophobe. Preferably the ratio will be from 0.2 moles to 3.0 moles glyoxal to each hydroxyl group, and most preferably this ratio will be between 0.4–2.0 moles glyoxal to each hydroxyl group.

Catalysis and Reaction Temperature

It is preferred that acid be used to catalyze the reaction. When concentrated sulfuric acid is used, the amount should range from 0.1–50% based on the weight of the glyoxal and hydrophobe combined. Reaction times generally range from 5 minutes to 6 hours.

Other acidic catalysts may be used in lieu of the sulfuric acid including mineral acids such as hydrochloric acid, organic acids such as p-toluene sulfonic acid and acid salts such as ferric chloride and zinc chloride.

The reaction temperature should be in the range of room temperature to 100° C. Preferably, the reaction temperature will be from room temperature to 80° C.

Application of Glyoxal-Hydrophobe Reaction Products

A preferable form of the internal sizing agent is as a fine particle size emulsion or suspensoid. The term colloid will be used herein to refer to both emulsions and suspensions of solids.

The glyoxal-hydrophobe reaction product lends itself well to emulsification in water. Colloids containing up to 40% of the glyoxal-hydrophobe reaction product can be prepared at the site of use or they can be prepared at the point of manufacture and shipped as ready-to-use products.

Those skilled in the art will recognize that certain additives such as protective colloids and surfactants will aid in producing stable, fine particle size aqueous colloids. Useful surfactants include polyethylene oxide adducts. Useful protective colloids include guar gum, locust bean gum, polyvinyl alcohol, and hydroxyethyl cellulose.

Optimal wet-end application of the glyoxal-hydrophobe reaction product requires use of binding agents to attract and bind the sizing composition to the pulp fibers. Various binding agents can be used including cationic agents, anionic agents and nonionic agents.

Useful cationic agents include cationic hydrocolloids such as cationic starches and cationic gums, cationic homopolymers such as diallyl dimethyl ammonium chloride polymer, diallyl amine polymer, ethylenimine polymer; cationic copolymers such as cationic acrylamide copolymers, cationic thermosetting resins, cationic epichlorohydrin-amine resins, cationic amino polyamides, ethylene dichloride-ammonia reaction products, long chain fatty amines and aluminum chloride. Useful anionic agents include anionic surfactants, anionic hydrocolloids such as anionic starches and carboxymethyl-cellulose and anionic polymers such as acrylamide-acrylic acid copolymers. Non-ionic agents include gums such as locust bean gum and guar gum.

The preferred binding agents include cationic starches, cationic epichlorohydrin-amine resins, cationic amino polyamides, ethylene dichloride-ammonia reaction products and polydiallyl dimethyl ammonium chloride.

When used for internal sizing, the glyoxal-hydrophobe reaction product in combination with a binding agent (sizing composition) is added to the aqueous pulp suspension at a point after refining is complete and prior to sheet formation. The sizing composition will generally be added to the pulp suspension as a dilute solution.

The preferred ratio of binding agent to glyoxal-hydrophobe reaction product for purposes of internal sizing will depend upon the nature of the binding agent. Generally, the ratio of the binding agent to the glyoxal-hydrophobe reaction product will be in the range of about 1:20 to 4:1.

We do not restrict ourselves as to manner of combination (of the size and binding agent). Thus, for example, they can both be incorporated in the colloidal sizing composition, or be added separately to the paper system for wet end application.

The amount of glyoxal-hydrophobe reaction product added to the aqueous pulp slurry will generally be from 1 to 30 pounds per ton based on the weight of dry cellulose fiber (0.05-1.5%). Efficient performance of internal sizing agents requires that the agents be well dispersed in the pulp slurry prior to formation of the paper sheet. This insures that the sizing agent will be uniformly distributed among the cellulose fibers of the dried paper sheet. Following addition of the sizing composition to the pulp furnish, the paper sheet is formed and dried.

The glyoxal-hydrophobe reaction product in combination with a binding agent as described above may be used in surface sizing as well as in internal sizing of paper. A cationic hydrocolloid such as a cationic starch would be a useful binder in such applications. The glyoxal-hydrophobe reaction product may also be used satisfactorily in surface sizing in the absence of a binding agent.

The surface size is applied in the conventional way during paper manufacture by treating the partially dried cellulose fibers. After treatment the sheet is dried to leave a residue on the paper surface. The dosage of the sizing composition should be from 0.05–1.0% based on the dry weight of the paper being surface sized.

EXAMPLES

Synthesis and testing work was carried out as described below to determine the efficacy of the invention.

Glyoxals used included a commercial grade of glyoxal solution of 40% concentration, this material concentrated to 70% by vacuum distillation, and a commercial grade of 80% glyoxal in solid form.

The sulfuric acid used was analytical grade concentrated sulfuric acid of 95–98% assay. As a matter of simplicity in much of the work, a commercial grade of cationic starch was used. For this purpose, the starch was cooked in water at 200° F. for 30 minutes and quenched to 3% or lower concentration.

To study preparation of colloidal emulsions, a laboratory hand homogenizer was used.

The examples below describe the preparation and evaluation of various sizing compositions falling within the teaching of the invention. Evaluations were carried out on paper, using handsheets prepared on a laboratory Noble & Wood sheet machine. A bleached softwood-hardwood blend of 50 seconds Williams slowness was used. The diluted size sample was added to the pulp slurry with mixing and a series of handsheets formed, pressed and dried on the drum drier.

Portions of the finished handsheets were set aside in a constant temperature-humidity room to permit aging studies. Sizing performance was evaluated with a Hercules Sizing Tester, with use of pH 7 or pH 2 ink. Sizing times as given are the intervals in seconds required to reduce reflectance to the 80% level.

For the surface sizing studies, a laboratory Keegan coater was used.

As given herewith, Examples 1 to 8 primarily concern variables of size preparation, formulation for paper application, and evaluation in paper application for use of aqueous glyoxal of 40% concentration. Examples 9 to 11 concern use of glyoxal of 40%, 70% and 80% concentration in size preparation and relative sizing performance of such compositions.

EXAMPLE 1

Sizing compositions were prepared from cetyl alcohol and glyoxal using variable sulfuric acid charge.

Six 50 gram portions of cetyl alcohol (0.2 mole) were placed in 8 ounce bottles on a 70° C. water bath equipped with mixers, melted and stirred continuously. 14.9 Grams of 40% glyoxal (0.1 mole) were slowly added to each portion. After an additional 15 minutes, increasing portions of sulfuric acid were added dropwise to this series.

The samples were stirred for an additional 90 minutes, removed from the bath and allowed to solidify. After 3 hours, the samples were placed on the bath and remelted without mixing. On remelting, distinct separation of the water phase occurred.

The water phase was removed and analyzed for glyoxal content. The fraction of the glyoxal retained in the organic phase was then calculated. The results are shown in Table I.

TABLE I

| Sample | $H_2SO_4$ Charge (Grams) | % of Glyoxal Retained in Alcohol Phase |
|---|---|---|
| 1(a) | 0 | 65.9 |
| 1(b) | 1.25 | 79.0 |
| 1(c) | 2.5 | 83.5 |
| 1(d) | 5 | 88.0 |
| 1(e) | 7.5 | 96.5 |
| 1(f) | 10 | 98 |

Two gram portions of (a), (d) and (f) were melted and blended with 100 cc of 2% cationic starch at 70° C., pH adjusted to 4 with dilute caustic, homogenized and allowed to cool. These products were therewith tested for internal sizing performance by preparation of Noble & Wood handsheets as earlier described. Application as size was 5 pounds per ton and papermaking pH was 7.6. Hercules size tests for pH 7 ink were conducted. The results are shown in Table II.

TABLE II

| Sample | Seconds Sizing |
|---|---|
| Blank (no size) | 0.15 |
| 1(a) | 0.4 |
| 1(d) | 83.4 |
| 1(f) | 71.0 |

Test results indicated that the $H_2SO_4$ promoted the reaction and enhanced the performance.

EXAMPLE 2

This example involves lower sulfuric acid catalysed levels. Fifty gram portions of octadecanol were melted and brought to 75° C. The samples were treated with increasing levels of concentrated sulfuric acid and mixed well for 5 minutes. They were then treated with 13.4 grams of 40% glyoxal and mixed well at 75° C. for 6 hours.

1.5 Gram portions of the products were homogenized in 100 cc of 3% cationic starch with pH adjustment to 4.0. These samples were then evaluated for internal sizing with papermaking pH 7.6, at the size level of 3.5 pounds per ton. The results are shown in Table III of a Hercules size test, using pH 7 ink.

TABLE III

| Sample | $H_2SO_4$ Charge (Grams) | Sizing Against pH 7 Ink (Seconds) |
|---|---|---|
| 3(a) | 0.10 | 0.3 |
| 3(b) | 0.20 | 3.1 |
| 3(c) | 0.42 | 200.4 |
| 3(d) | 0.84 | 200.2 |
| 3(e) | 1.68 | 215.4 |

EXAMPLE 3

For use of octadecanol, shorter reaction times than those of Example 2 were studied. Two 50 gram portions of octadecanol were each melted and brought to 75° C. The samples were then treated with 0.418 grams of concentrated sulfuric acid and mixed well for 5 minutes. The 2 samples were then treated with 13.4 grams of 40% glyoxal and mixed well at 75° C. over periods of 2 hours and 1 hour respectively.

1.5 Gram portions of the products were homogenized in 100 cc of 3% cationic starch with pH adjustment to 4.0. These samples were then evaluated for internal sizing with a papermaking pH at 7.6, at the size level of 3.5 pounds per ton. The results are shown in Table IV of a Hercules size test using pH 7 ink.

TABLE IV

| Sample | Reaction Time Hours | Sizing Against pH 7 Ink (Seconds) |
|---|---|---|
| 4(a) | 1 | 137.4 |
| 4(b) | 2 | 144.2 |

EXAMPLE 4

This series of tests concerned glyoxal charge for otherwise fixed conditions, for use of 40% glyoxal.

Five 50 gram portions of cetyl alcohol were melted on a 70° C. water bath as in Example 1. Increasing charges of 40% glyoxal were added to the 5 samples, followed by 5 grams of concentrated $H_2SO_4$. The samples were mixed well for 1 hour at 70° C. following $H_2SO_4$ addition.

The samples were then removed from the water bath and further treated as in Example 1 to separate the water phase. Analysis of the water phase in each case for remaining glyoxal permits calculation of the amount taken up in the reaction into the organic phase. The results are given in Table V.

TABLE V

| Sample | 40% Glyoxal Charge | % of Glyoxal Retained in Alcohol Phase |
|---|---|---|
| 5(a) | 11.2 grams | 96.8 |
| 5(b) | 14.9 grams | 89.9 |
| 5(c) | 18.7 grams | 85.3 |
| 5(d) | 22.4 grams | 75.3 |
| 5(e) | 29.9 grams | 65.3 |

Samples of the glyoxal-alcohol compositions were homogenized in the cooked cationic starch as in Example 1. However, for this series, the ratio of cationic starch to size was increased to 2:1. The samples were evaluated for internal sizing as in Example 1, except that the level of size application was reduced from 5 to 3.5 pounds per ton. The results are given in Table VI.

TABLE VI

| Sample | Seconds Sizing For pH 7 Ink |
|---|---|
| 6(a) | 26.9 |
| 6(b) | 92.0 |
| 6(c) | 105.0 |
| 6(d) | 109.2 |
| 6(e) | 109.2 |

These results show that within limits the level of glyoxal is not extremely critical.

EXAMPLE 5

This series of tests demonstrates the effect of alcohol chain length on the properties of the compositions when used as internal sizes. Six substantially pure commercially available alcohols, and three industrial blends were used:

Alcohols: octanol, decanol, dodecanol, tetradecanol, hexadecanol (cetylalcohol), and octadecanol.

Blends: Alfol 14-18 DDB; a blend of $C_{14}$-$C_{18}$ linear alcohols. Alfol 16-20H+; a blend of $C_{16}$-$C_{20}$ linear alcohols. Alfol 20+; a blend containing about 74% of $C_{20}$-$C_{28}$ alcohols.

The blends were obtained from Conoco Chemicals Division, Continental Oil Company.

The sizing compositions were prepared by bringing the alcohol to 75° C. on a water bath, and then adding, with good mixing, 0.5 moles of 40% glyoxal solution per mole of alcohol. After an additional 15 minutes, concentrated sulphuric acid was slowly added in an amount equal to 25% by weight of the added glyoxal solution. The samples were maintained at 75° C. for 1 hour after completion of the acid addition, and then removed from the bath. Samples were then homogenized in cooked cationic starch, neutralized to pH 4 dilute sodium hydroxide), and allowed to cool.

The samples were evaluated for papermaking at a pH of 7.6, by using a Hercules sizing test using a pH 7 ink. The results are shown in Table VII.

TABLE VII

| Sample No. | Alcohol in Sizing Composition | Application Rate, pounds/ton | Seconds Sizing, pH 7 Ink |
|---|---|---|---|
| 7(a) | Octanol | 6.0 | 0.35 |
| 7(b) | Decanol | 6.0 | 52.0 |
| 7(c) | Dodecanol | 6.0 | 127.6 |
| 7(d) | Tetradecanol | 3.5 | 57.8 |
| 7(e) | Hexadecanol | 3.5 | 76.2 |
| 7(f) | Octadecanol | 3.5 | 124.3 |
| 7(g) | Alfol 14-18 DDB | 3.5 | 55.0 |
| 7(h) | Alfol 16-20H+ | 3.5 | 83.0 |
| 7(i) | Alfol 20+ | 3.5 | 10.5 |

EXAMPLE 6

This example illustrates the preparation and evaluation of a sizing composition using a sorbitan ester of a fatty acid. For this purpose sorbitan tristearate (sold commercially as Span 65, a product of ICI America, Inc.) was used.

50 Grams of the sorbitan tristearate were melted on a 75° C. bath. With good mixing, 6.45 grams of 40% glyoxal and 1.25 grams of sulfuric acid were added. The blend was stirred for 1 hour and removed from the bath. 1.5 Grams of the composition was blended with 100 cc of 3% cooked cationic starch at 75° C., homogenized and pH adjusted to pH 4.0.

The product was then evaluated as in earlier studies for internal sizing performance. At 5 pounds per ton size, sizing was 4.4 seconds against pH 7 ink.

EXAMPLE 7

For wet end paper application, earlier examples have involved homogenizing the sizing compositions at low concentration, below 3% concentration, in cooked cationic starch solutions. For commercial use, preparation of the finished product at such low concentration is generally less attractive than preparation at higher colloid concentration.

This example illustrates the preparation of a sizing composition at a higher concentration than practiced in earlier examples, the incorporation of a cationic resin instead of cationic starch, the use of surfactants to facilitate product preparation, and use of a protective colloid to stabilize the finished product.

In a pilot plant operation, 12 pounds of Alfol 16-20H+ alcohol (Conoco) was melted in a kettle and heated to 80° C. With moderate mixing, 120 grams of 96% sulfuric acid was added. Four pounds of 40% glyoxal was added, and the composition mixed at 73°-80° C. for 2 hours. It was allowed to cool to 70° C. Meanwhile, a blend of 18.8 pounds of distilled water, 134 grams of Igepal C0977 surfactant and 31 grams of Igepal C0660 surfactant were heated to 70° C. They were charged to the above melt and mixed for 10 minutes. Therewith, 6 pounds (active basis) of a resin solution prepared by reacting epichlorohydrin, dimethyl amine and ammonia in an aqueous phase, with final addition of hydrochloric acid (see column 5, lines 16-75 of U.S. Pat. No. 3,738,945) was added, with continued stirring. Temperature fell to 60° C. Therewith, 348 grams of 50% sodium hydroxide was slowly added, to raise the pH to 5.0. This composition at 60°-57° was homogenized in a Manton-Gaulin homogenizer at 1500 p.s.i. pressure and run into a 0.4% guar gum solution at room temperature with mild stirring to provide a final product of 30.6% solids concentration. This colloidal concentrate gave good sizing in laboratory handsheet preparation and had good shelf life on aging.

EXAMPLE 8

This example illustrates use of the sizing compositions of the invention in surface sizing of paper. The sizing composition in Example 7 was used.

A hydroxyethylated starch was batch cooked at 10% concentration in water and cooled to 140° F. The starch was then split into 4 portions of 500 cc each. Three of the portions were treated with increasing levels of the size concentrate.

A commercial 45 pound offset paper grade was then treated with the above 4 portions in a Keegan coater to simulate size press application at starch level of 100 pounds per ton. The treated paper was dried on a drum-drier, conditioned in a constant temperature-humidity room and evaluated for sizing against pH 7 and pH 2 inks. The results are shown in Table VIII.

TABLE VIII

|  | Hercules Sizing Tests, Seconds | |
|---|---|---|
|  | pH 7 Ink | pH 2 Ink |
| Starch alone | 24.1 | 10.7 |
| Starch + 2.5 pounds per ton size | 28.0 | 13.3 |
| Starch + 5 pounds per ton size | 58.2 | 38.3 |
| Starch + 10 pounds per ton size | 100.0 | 83.6 |

EXAMPLE 9

Herewith, use of glyoxal of 80% concentration is compared to use of glyoxal of 40% concentration. Sizing compositions were prepared with the following molar ratios of reagents:

TABLE IX

|  | GLYOXAL CONCENTRATION | GLYOXAL MOLES | ALFOL 16-20H+ ALCOHOL, MOLES | SULFURIC ACID, MOLES |
|---|---|---|---|---|
| (a) | 40% | 1.0 | 1.6 | 0.096 |
| (b) | 80% | 1.0 | 1.6 | 0.096 |
| (c) | 80% | 1.0 | 1.0 | 0.096 |
| (d) | 80% | 1.0 | 0.5 | 0.096 |

We note that in earlier work with 40% glyoxal (Example 4), a range of glyoxal levels are studied.

In preparation of the sizing composition, the alcohol was melted, the sulfuric acid added, the glyoxal solution or solid added with vigorous stirring, and the reaction maintained at 75°–85° C. for 90 minutes.

In contrast to earlier sizing evaluations, these preparations were dissolved in chloroform at 1% size concentration, unsized paper was immersed in this solution for 30 seconds, and the paper dried on a drum drier, and evaluated for surface sizing, with results as follows:

TABLE X

| | GLYOXAL USED | MOLAR RATIO ALCOHOL TO GLYOXAL | SIZING (SECONDS) pH 7 INK | pH 2 INK |
|---|---|---|---|---|
| (a) | 40% | 1.6:1 | 329 | 390 |
| (b) | 80% | 1.6:1 | 275 | 893 |
| (c) | 80% | 1:1 | 382 | 1038 |
| (d) | 80% | 0.5:1 | 352 | 3018 |

The 80% glyoxal reaction product gave appreciably higher pH 2 ink sizing than did the 40% glyoxal product. In the 80% glyoxal case, pH 2 ink sizing increased appreciably with increasing glyoxal to alcohol ratio.

EXAMPLE 10

The sizing compositions from Example 9 were formulated for, and evaluated in wet end sizing. Preparation of the cationic colloids was generally as described in Example 7, but on a smaller scale, with hand-homogenizing. A slightly different surfactant formulation was used. Overall composition was as follows:
18.8% sizing composition
21.8% soft water
0.24% Ethomeen 18/60 surfactant
0.08% Igepal CO-660 surfactant
14.7% cationic resin solution
0.9% 50% caustic
44.3% 0.4% guar gum solution
Wet end sizing evaluation gave results as follows for papermaking at pH 7.6.

TABLE XI

| SIZE APPLICATION POUNDS/TON | SIZE PREPARATION | | SIZING PERFORMANCE SECONDS | |
|---|---|---|---|---|
| | GLYOXAL CONCENTRATION | MOLAR RATIO ALCOHOL TO GLYOXAL | pH 7 INK | pH 2 INK |
| 6 | 40% | 1.6:1 | 100 | 170 |
| 6 | 80% | 1.6:1 | 250 | 394 |
| 6 | 80% | 0.5:1 | 270 | 890 |
| 8 | 40% | 1.6:1 | 160 | 500 |
| 8 | 80% | 0.5:1 | 390 | 1800 |
| 10 | 40% | 1.6:1 | 270 | 680 |
| 10 | 80% | 0.5:1 | 480 | 2400 |

From this wet end sizing study, two significant points are as follows:
(a) when glyoxal of 40% concentration was replaced by glyoxal of 80% concentration in the initial sizing composition, appreciably superior sizing performance was realized
(b) when the ratio of 80% glyoxal to fatty alcohol was increased further, significant improvements in sizing were realized.

EXAMPLE 11

A glyoxal solution of 70% concentration was prepared by vacuum-stripping a 40% glyoxal solution in a rotary evaporator. This glyoxal was reacted with Alfol 16–20 H+ alcohol and sulfuric acid at a 1.6 mole alcohol to 1.0 mole glyoxal ratio as described in Example 9, and emulsified for wet end application as described in Example 10. It was applied at 6 pounds per ton in wet end application. pH 7 ink sizing was 180 seconds and pH 2 ink sizing 482 seconds, distinctly superior to that obtained for use of glyoxal of 40% concentration, as given in Example 10.

Thus, Examples 10 and 11 show distinctly superior wet end sizing performance for use of glyoxal of 70% and 80% concentration than for use of glyoxal of 40% concentration in size preparation.

Earlier, J. M. Kliegman and R. K. Barnes (J. Org. Chem., Vol. 38, p. 556, 1973) studied reactions of relatively low molecular weight alcohols (methanol to 2-ethyl hexanol) with glyoxal. Herewith, compositions of our acid-catalyzed fatty alcohol-glyoxal reaction products is considered. We performed NMR analyses on the following reaction products from Example 9:

(a) 40% glyoxal-1.6 moles Alfol, 0.096 mole $H_2SO_4$, 1.0 mole glyoxal (b) 80% glyoxal-1.6 moles Alfol, 0.096 mole $H_2SO_4$, 1.0 mole glyoxal (d) 80% glyoxal-0.5 mole Alfol, 0.096 mole $H_2SO_4$, 1.0 mole glyoxal and on a purified tetra-alkoxy ethane.

The following structures were confirmed:

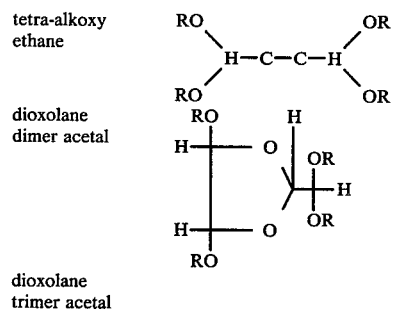

tetra-alkoxy ethane dioxolane dimer acetal dioxolane trimer acetal

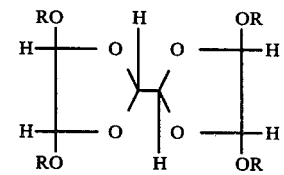

wherein R represents a fatty alkyl group.

From the NMR studies and from Examples 9 and 10, the following table shows the relations of initial size formulation, composition of the size and wet end sizing performance.

TABLE XII

| GLYOXAL CONCN. | MOLAR RATIO ALCOHOL-GLYOXAL | COMPOSITION AS DETERMINED BY NMR | WET END SIZING | | |
|---|---|---|---|---|---|
| | | | APPLICATION POUNDS PER TON | PERFORMANCE (SECONDS) | |
| | | | | pH 7 INK | pH 2 INK |
| 40% | 4:1 [1] | tetra-alkoxy ethane | relatively poor performance | | |
| 40% | 1.6:1 | tetra-alkoxy ethane and probably dioxolane oligomer | 6 | 100 | 170 |
| | | | 8 | 160 | 500 |
| | | | 10 | 270 | 680 |
| 80% | 1.6:1 | alkoxy dioxolane dimer and trimer, with little monomer | 6 | 250 | 394 |
| 80% | 0.5:1 | alkoxy dioxolane dimer and trimer | 6 | 270 | 890 |
| | | | 8 | 390 | 1800 |
| | | | 10 | 480 | 2400 |

[1] specially-prepared tetra-alkoxy ethane.

From the NMR and paper sizing studies, higher sizing performance corresponds to predominantly higher proportions of alkoxy dioxolanes and possibly alkoxy-hydroxy dioxolanes and lower proportions of alkoxy monomer and alkoxy-hydroxy monomer in the sizing composition.

What is claimed is:

1. A composition for sizing paper comprising the acid catalysed reaction product of an aqueous solution of glyoxal containing no less than 40 wt % and no more than 80 wt % glyoxal, and a hydrophobe chosen from the group consisting of:
   (A) linear and branched, saturated and unsaturated fatty alcohols containing from 10 to 30 carbon atoms, and mixtures of such alcohols; and
   (B) esters of polyols containing from 2 to 5 carbon atoms with fatty acids containing from 10 to 30 carbon atoms which esters contain at least one free hydroxyl group, and mixtures of such esters;
and wherein from 0.1 mole to 3.0 moles of glyoxal is used per hydroxyl group in the hydrophobe.

2. A composition according to claim 1 additionally containing an ionic binding agent.

3. A composition according to claim 2 wherein the binding agent is chosen from the group consisting of cationic starches, cationic epichlorohydrin-amine resins, cationic amino polyamides, ethylene dichloride-ammonia reaction products and polydiallyl dimethyl ammonium chloride.

4. A composition according to claim 3 wherein the binding agent is cationic starch.

5. A composition according to claim 2, 3, or 4 wherein the ratio of the binding agent to the glyoxal-hydrophobe reaction product is from about 1:20 to about 4:1.

6. A composition according to claim 1 wherein the hydrophobe is chosen from the group consisting of linear and branched, saturated and unsaturated fatty alcohols containing from 10 to 30 carbon atoms and mixtures of such alcohols.

7. A composition according to claim 1 wherein the hydrophobe is chosen from the group consisting of decanol, dodecanol, tetradecanol, hexadecanol and octadecanol.

8. A composition according to claim 1 wherein the hydrophobe is a mixture of linear alcohols having 14 to 18 carbon atoms.

9. A composition according to claim 1 wherein the hydrophobe is a mixture of linear alcohols having 16 to 20 carbon atoms.

10. A composition according to claim 1 wherein the hydrophobe is a mixture of long chain alcohols containing a major proportion of alcohols having 20 to 28 carbon atoms.

11. A composition according to claim 1 containing a reaction product derived from a 40 wt % glyoxal solution.

12. A composition according to claim 1 containing a reaction product derived from a 70 wt % glycol solution.

13. A composition according to claim 1 containing a reaction product derived from a 80 wt % glyoxal solution.

14. Paper consisting of cellulose fibers containing the dried residue of the composition of claim 1.

15. A process for the preparation of a paper sizing composition which comprises reacting an aqueous solution containing not less than 40 wt % and not more than 80 wt % of glyoxal in the presence of an acidic catalyst with a hydrophobe chosen from the group consisting of:
   (A) linear and branched, saturated and unsaturated fatty alcohols containing from 10 to 30 carbon atoms and mixtures of such alcohols; and
   (B) esters of polyols containing from 2 to 6 carbon atoms with fatty acids containing 10 to 30 carbon atoms, which esters contain at least one free hydroxyl group, and mixtures of such esters,
wherein the reaction mixture contains from 0.1 mole to 3.0 moles of glyoxal per hydroxyl group in the hydrophobe; and thereafter separating the reaction product from the mixture.

16. A process according to claim 15 wherein the aqueous solution of glyoxal contains 40 wt % glyoxal.

17. A process according to claim 15 wherein the aqueous solution of glyoxal contains 70 wt % glyoxal.

18. A process according to claim 15 wherein the aqueous solution of glyoxal contains 80 wt % glyoxal.

19. A process according to claim 15 wherein the acid catalyst is chosen from the group consisting of mineral acids, organic sulfonic acids and acid reacting inorganic salts.

20. A process according to claim 19 wherein the acid catalyst is chosen from the group consisting of sulfuric acid, hydrochloric acid, p-toluene sulphonic acid, ferric chloride and zinc chloride.

21. A process according to claim 19 wherein the acid catalyst is sulphuric acid or hydrochloric acid.

22. A process according to claim 15 wherein the hydrophobe is chosen from the group consisting of linear and branched, saturated and unsaturated fatty alcohols containing from 10 to 30 carbon atoms and mixtures of such alcohols.

23. A process according to claim 15 wherein the hydrophobe is chosen from the group consisting of decanol, dodecanol, tetradecanol, hexadecanol and octadecanol.

24. A process according to claim 15 wherein the hydrophobe is a mixture of linear alcohols having 14 to 18 carbon atoms.

25. A process according to claim 15 wherein the hydrophobe is a mixture of linear alcohols having 16 to 20 carbon atoms.

26. A process according to claim 15 wherein the hydrophobe is a mixture of long chain alcohols containing a major proportion of alcohols having 20 to 28 carbon atoms.

27. In a process for sizing paper by applying thereto a sizing composition including a sizing agent, the improvement comprising using as the sizing composition the acid catalysed reaction product of an aqueous solution of glyoxal containing no less than 40 wt % and no more than 80 wt % glyoxal, and a hydrophobe chosen from the group consisting of:
   (A) linear and branched, saturated and unsaturated fatty alcohols containing from 10 to 30 carbon atoms, and mixtures of such alcohols; and
   (B) esters of polyols containing from 2 to 6 carbon atoms which fatty acids containing from 10 to 30 carbon atoms which esters contain at least one free hydroxyl group, and mixtures of such esters;
and wherein from 0.1 mole to 3.0 moles of glyoxal is used per hydroxyl group in the hydrophobe.

28. A process according to claim 27 wherein the sizing composition contains a reaction product derived from a 40 wt % glyoxal solution.

29. A process according to claim 27 wherein the sizing composition contains a reaction product derived from a 70 wt % glyoxal solution.

30. A process according to claim 27 wherein the sizing composition contains a reaction product derived from a 80 wt % glyoxal solution.

31. A process according to claim 27 wherein the sizing composition additionally includes a binding agent.

32. A process according to claims 31 or 27 wherein the hydrophobe is chosen from the group consisting of linear and branched, saturated and unsaturated fatty alcohols containing from 10 to 30 carbon atoms and mixtures of such alcohols.

33. A process according to claims 31 or 27 wherein the hydrophobe is chosen from the group consisting of decanol, dodecanol, tetradecanol, hexadecanol and octadecanol.

34. A process according to claims 31 or 27 wherein the hydrophobe is a mixture of linear alcohols having 14 to 18 carbon atoms.

35. A process according to claims 31 or 27 wherein the hydrophobe is a mixture of linear alcohols having 16 to 20 carbon atoms.

36. A process according to claims 31 or 27 wherein the hydrophobe is a mixture of long chain alcohols containing a major proportion of alcohols having 20 to 28 carbon atoms.

37. A process according to claim 31 wherein the binding agent is cationic starch.

38. A process according to claim 31 wherein the ratio of the binding agent to the glyoxal-hydrophobe reaction product is from about 1:20 to about 4:1.

39. A process according to claim 31 or 27 wherein the sizing composition is applied as an internal size.

40. A process according to claims 31 or 27 wherein the sizing composition is applied as an external size.

41. A process according to claims 31 or 27 wherein the sizing composition is applied as an aqueous emulsion including, in addition to the glyoxal-hydrophobe reaction product, a surfactant and a protective colloid.

* * * * *

UNITED STATES PATENT OFFICE
CERTIFICATE OF CORRECTION

Patent No. 4,295,930           Dated OCTOBER 20, 1981

Inventor(s) THOMAS AITKEN, DAVID J. KOWALSKI & K. G. SRINIVASAN

It is certified that error appears in the above-identified patent and that said Letters Patent are hereby corrected as shown below:

A-" COLUMN 10, LINE 30."
THE FORMULA FOR THE TETRA-ALKOXY ETHANE NOW READING:

tetra-alkoxy ethane
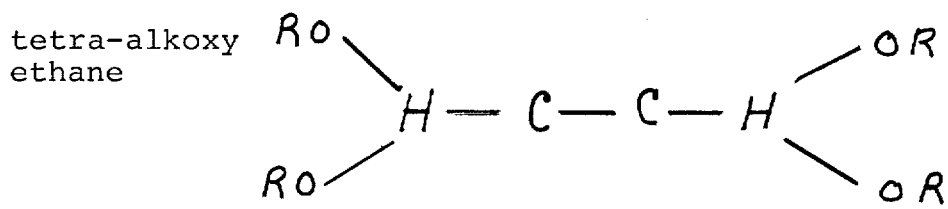

A-"LETTERS PATENT SHOULD READ AS:"

tetra-alkoxy ethane
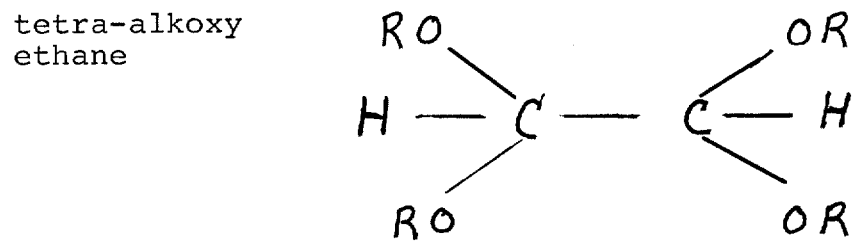

B-COLUMN 10 LINE 40, THE PHRASE "DIOXOLANE TRIMER ACETAL"

UNITED STATES PATENT AND TRADEMARK OFFICE
CERTIFICATE OF CORRECTION

PATENT NO. : 4,295,930

DATED : October 20, 1981

INVENTOR(S) : THOMAS AITKEN, DAVID J. KOWALSKI & K. G. SRINIVASAN

It is certified that error appears in the above—identified patent and that said Letters Patent is hereby corrected as shown below:

SHOULD APPEAR ADJACENT TO THE FORMULA AT LINE 60.

Signed and Sealed this

Thirteenth Day of April 1982

[SEAL]

Attest:

GERALD J. MOSSINGHOFF

Attesting Officer

Commissioner of Patents and Trademarks